(12) United States Patent
Ashton et al.

(10) Patent No.: US 8,277,514 B2
(45) Date of Patent: Oct. 2, 2012

(54) FIXING ASSEMBLY

(75) Inventors: Roger William Frank Ashton, Stoulton (GB); Derek James Wallace McMinn, Birmingham (GB)

(73) Assignee: T. J. Smith & Nephew Limited (GB)

( * ) Notice: Subject to any disclaimer, the term of this patent is extended or adjusted under 35 U.S.C. 154(b) by 0 days.

(21) Appl. No.: 13/023,700

(22) Filed: Feb. 9, 2011

(65) Prior Publication Data

US 2011/0126403 A1 Jun. 2, 2011

Related U.S. Application Data

(62) Division of application No. 10/559,950, filed on Nov. 8, 2006, now Pat. No. 7,947,083.

(30) Foreign Application Priority Data

Jun. 11, 2003 (GB) .................................. 0313444.2
Jun. 11, 2004 (WO) ................ PCT/GB2004/002539

(51) Int. Cl.
*A61F 2/34* (2006.01)

(52) U.S. Cl. .................................. 623/22.36; 623/22.38

(58) Field of Classification Search ............... 623/16.11, 623/18.11, 19.11–19.13, 20.15, 20.34, 20.36, 623/22.21–22.46, 23.47
See application file for complete search history.

(56) References Cited

U.S. PATENT DOCUMENTS

| 3,787,132 | A |  | 1/1974 | Garnett |
| 4,666,450 | A | * | 5/1987 | Kenna ......................... 623/22.28 |
| 4,919,675 | A |  | 4/1990 | Dietschi |
| 5,176,711 | A |  | 1/1993 | Grimes |
| 5,192,329 | A |  | 3/1993 | Christie et al. |
| 5,226,917 | A | * | 7/1993 | Schryver ..................... 623/22.37 |
| 5,326,368 | A |  | 7/1994 | Collazo |
| 5,358,527 | A |  | 10/1994 | Forte |
| 5,549,692 | A |  | 8/1996 | Hauser et al. |
| 5,607,426 | A |  | 3/1997 | Ralph et al. |
| 5,871,548 | A |  | 2/1999 | Sanders et al. |
| 5,888,204 | A |  | 3/1999 | Ralph et al. |
| 6,162,257 | A |  | 12/2000 | Gustilo et al. |
| 6,416,553 | B1 |  | 7/2002 | White et al. |
| 6,454,809 | B1 |  | 9/2002 | Tornier |
| 6,475,241 | B2 |  | 11/2002 | Pappas |

(Continued)

FOREIGN PATENT DOCUMENTS

EP 0402810 12/1990

(Continued)

OTHER PUBLICATIONS

Office Action dated Mar. 27, 2009 in Australian Application No. 2004244820.

(Continued)

*Primary Examiner* — Brian Pellegrino
*Assistant Examiner* — Megan Wolf
(74) *Attorney, Agent, or Firm* — Kilpatrick Townsend & Stockton LLP

(57) ABSTRACT

A component, e.g. a prosthetic ball and socket joint like an acetabular cup of a prosthetic joint, having a male or female location feature in a surface thereof for mutual interfit with a fixing member of a fixing assembly for securing the fixing member to the surface of the component and optionally for securing the component to a second component by means of a fixing screw.

24 Claims, 3 Drawing Sheets

U.S. PATENT DOCUMENTS

| | | |
|---|---|---|
| 6,575,975 B2 | 6/2003 | Brace et al. |
| 7,291,177 B2 * | 11/2007 | Gibbs ................... 623/22.25 |
| 2003/0097183 A1 * | 5/2003 | Rauscher et al. .......... 623/19.13 |
| 2004/0199258 A1 | 10/2004 | Macara |
| 2005/0216011 A1 | 9/2005 | Paul |
| 2006/0058887 A1 | 3/2006 | DeSmet et al. |
| 2007/0093133 A1 | 4/2007 | Ashton et al. |
| 2008/0021568 A1 | 1/2008 | Tulkis et al. |
| 2009/0204225 A1 | 8/2009 | Meridew et al. |
| 2009/0326670 A1 | 12/2009 | Keefer et al. |

FOREIGN PATENT DOCUMENTS

| | | |
|---|---|---|
| EP | 0551794 | 7/1993 |
| EP | 0605368 | 7/1994 |
| EP | 1236450 | 9/2002 |
| FR | 2578162 | 9/1986 |
| FR | 2758255 | 7/1998 |
| FR | 2827503 | 1/2003 |
| FR | 2882921 | 9/2006 |
| FR | 2883722 | 10/2006 |
| JP | 10201779 | 8/1998 |
| WO | WO02083035 | 10/2002 |
| WO | WO03013397 | 2/2003 |
| WO | WO2004108020 | 12/2004 |

OTHER PUBLICATIONS

Office Action dated Jul. 28, 2009 in Japanese Patent Application No. 2006-516419.

Office Action dated Aug. 7, 2008 in European Patent Application No. 04736652.1.

Office Action dated Aug. 14, 2007 in European Patent Application No. 04736652.1.

Office Action dated Sep. 10, 2010 in Canadian Application No. 2527883.

*Office Action dated Nov. 7, 2007 in parent U.S. Appl. No. 10/559,950.

*Response dated Feb. 4, 2008 in parent U.S. Appl. No. 10/559,950.

*Office Action dated Jul. 17, 2008 in parent U.S. Appl. No. 10/559,950.

*Response dated Oct. 17, 2008 in parent U.S. Appl. No. 10/559,950.

*Office Action dated Jan. 15, 2009 in parent U.S. Appl. No. 10/559,950.

*Response dated Feb. 12, 2009 in parent U.S. Appl. No. 10/559,950.

*Office Action dated May 21, 2009 in parent U.S. Appl. No. 10/559,950.

*Response dated Jul. 23, 2009 in parent U.S. Appl. No. 10/559,950.

*Office Action dated Sep. 25, 2009 in parent U.S. Appl. No. 10/559,950.

*Response dated Nov. 16, 2009 in parent U.S. Appl. No. 10/559,950.

*Notice of Allowance dated Dec. 2, 2009 in parent U.S. Appl. No. 10/559,950.

*RCE dated Mar. 1, 2010 in parent U.S. Appl. No. 10/559,950.

*Office Action dated Nov. 9, 2010 in parent U.S. Appl. No. 10/559,950.

*Response dated Feb. 9, 2011 in parent U.S. Appl. No. 10/559,950.

*Notice of Allowance dated Mar. 17, 2011 in parent U.S. Appl. No. 10/559,950.

* cited by examiner

FIXING ASSEMBLY

CROSS-REFERENCE TO RELATED APPLICATIONS

This application is a divisional application of U.S. application Ser. No. 10/559,950 filed Nov. 8, 2006 entitled "Fixing Assembly," now U.S. Pat. No. 7,947,083 which claims priority to PCT Application No. PCT/GB04/02539 filed Jun. 11, 2004 entitled "Fixing Assembly," which claims priority to GB Application No. 0313444.2 filed Jun. 11, 2003, the contents of all of which are incorporated herein by this reference.

SUMMARY

Embodiments relate to a fixing assembly for securing a fixing member to a surface of a component, and particularly, but not exclusively, to a fixing assembly for securing a fixing member to a prosthetic cup fitted during the resurfacing or replacement of the bearing surfaces of a patient's hip joint.

Conventionally, during the resurfacing or replacement of the bearing surfaces in a hip joint, a standard prosthetic cup component is driven into a prepared location in the acetabulum, and the stability of the cup within the acetabulum assessed by the Surgeon. Occasionally, the stability of the cup within the acetabulum is judged to be inadequate, indicating that there would be insufficient bone fully to support the cup during the healing period. In these circumstances, the Surgeon may decide that the standard cup is to be removed, and a dysplasia cup having a number of integral fixing members fitted in its place. The integral support lugs are drilled and tapped to allow dysplasia support screws to be fitted. These support screws are then anchored into prepared points in the acetabulum. It can be seen that a disadvantage of such a method is that the Surgeon has to fit and then remove the standard cup before the dysplasia cup is fitted. It would be advantageous to provide a standard acetabular cup, to which support lugs may be fitted when required, thus allowing for the transformation of a standard acetabular cup into a dysplasia cup, thereby obviating the need to remove a standard cup.

A further disadvantage associated with dysplasia cups having integral fixing members, is that the location and angular disposition of the support screws is dictated by the location and orientation of the integral fixing members, and thus cannot be adjusted by the Surgeon. It would be desirable for the Surgeon to be able to adjust the location and/or the angle of the support screws in order to achieve the best fixation of the screws, and thus of the cup, in the acetabulum.

It is an object of the present invention to provide an improved fixing assembly.

According to a first aspect of the present invention, there is provided a fixing assembly for securing a fixing member to an external surface of a component, said fixing assembly comprising said surface of the component, a fixing member and a fixing screw, said surface and said fixing member being formed with a female location feature and a male location feature respectively, or vice versa, such that in use, said male and female location features fit together, and said fixing screw passes through an aperture in said fixing member to secure said fixing member to said surface, with said fixing screw being external to said surface.

According to a second aspect of the present invention, there is provided a fixing assembly for securing a fixing member to a surface of a component, said fixing assembly comprising said surface of the component, a fixing member and a fixing screw, said surface and said fixing member being formed with a female location feature and a male location feature respectively, or vice versa, such that in use, said male and female location features fit together, and said fixing screw passes through an aperture in said fixing member to secure said fixing member to said surface, with said fixing screw being available for securing said component to a second component.

Preferably, said male and female location features each have at least one corresponding undercut, and desirably, said male and female location features each have two corresponding such undercuts, so that in use, an interference fit dovetail joint is formed between said male and female locating features. Advantageously, the location feature of the component is at least partly located on a rim of said surface.

Preferably, said male location feature has a slit, such that the male location feature is divided into two arms. Advantageously, said slit allows deformation of the male location feature upon the interference fitting of the male and female location features, and desirably said male location feature is of resiliently deformable material.

Preferably, the male location feature having a slit is located on the fixing member, and desirably, said fixing member is formed such that the slit extends radially from the aperture, through said male location feature. Conveniently, said slit is formed in a plane substantially parallel to the axis of the aperture. Alternatively, the slit may be formed in a plane substantially perpendicular to the axis of the aperture.

Preferably, in use, when said fixing screw is screwed into said fixing member aperture, the arms of the male location feature are locked in position. Advantageously, when the fixing screw is partly or fully screwed out of said fixing member aperture, the orientation of the location feature of the fixing means relative to the location feature of the surface, and thus the orientation of the fixing means itself in relation to the surface, may be adjusted.

Preferably, said fixing screw has a head, and said screw has a thickened portion near the head, such that when the screw is screwed into the aperture of said male fixing member having at least one male location feature with a slit, the arms of the location feature are pushed apart.

Conveniently, said surface has a threaded portion adjacent the at least one location feature, such that, in use, as said fixing screw is screwed into said aperture of the fixing member, said fixing screw engages with said threaded portion.

Preferably, said surface has a circumferential groove forming said female location feature to lock the fixing member to the component.

According to a third aspect of the present invention, there is provided a kit of parts for a fixing assembly for securing a fixing member to an external surface of a component, the kit comprising an external surface of a component, a fixing member and a fixing screw, said surface and said fixing member being formed with a female location feature and a male location feature respectively, or vice versa, such that when the kit of parts is assembled, said male and female location features fit together, and said fixing screw passes through an aperture in said fixing member to secure said fixing member to said surface, with said fixing screw being external to said surface.

According to a fourth aspect of the present invention, there is provided a kit of parts for a fixing assembly for securing a fixing member to a surface of a component, the kit comprising a surface of a component, a fixing member and a fixing screw, said surface and said fixing member being formed with a female location feature and a male location feature respectively, or vice versa, such that when the kit of parts is assembled, said male and female location features fit together, and said fixing screw passes through an aperture in said fixing member to secure said fixing member to said surface, with said fixing screw being available for securing said component to a second component.

Preferably, said surface of a component is the external surface of a cup of a prosthetic ball and socket joint, and advantageously, said cup is an acetabular cup of a prosthetic hip joint. More preferably, said acetabular cup is a dysplasia cup. Desirably, said second component is bone.

According to a fifth aspect of the present invention, there is provided a component having a male or female location feature in a surface thereof, for mutual interfit with a fixing member of a fixing assembly of the first or second aspects of the present invention. Preferably, said component of said fifth aspect is an acetabular cup.

BRIEF DESCRIPTION OF THE DRAWINGS

The present invention will now be described, by way of example only, with reference to the accompanying drawings, in which:

FIGS. 11 to 13 are views corresponding to FIGS. 1 to 3 respectively, and FIG. 14 is an enlarged fragmentary schematic longitudinal view of the fixing assembly in use, showing detail of the female location feature of the cup, male location feature of the fixing member, and fixing screw of FIGS. 11 to 13.

DETAILED DESCRIPTION OF THE EMBODIMENTS

Figure 1:
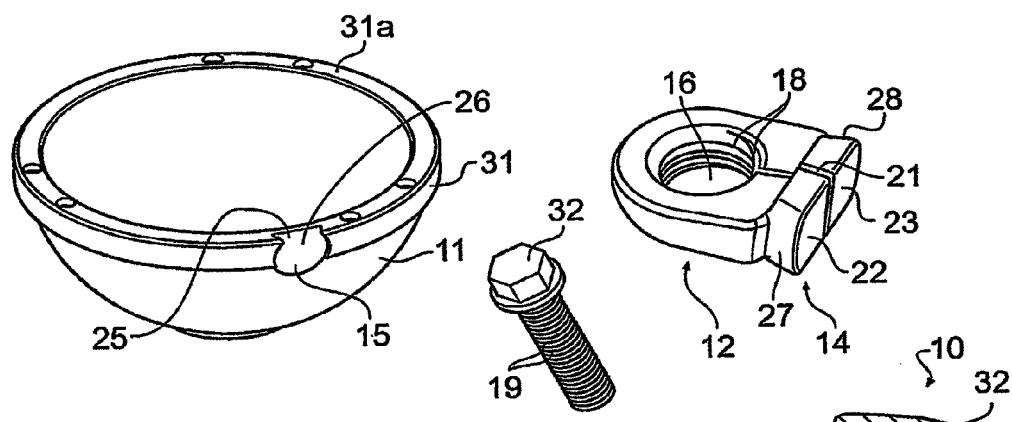
FIG. 1 is an exploded perspective view of a fixing assembly according to a first embodiment of the present invention
Figure 2:
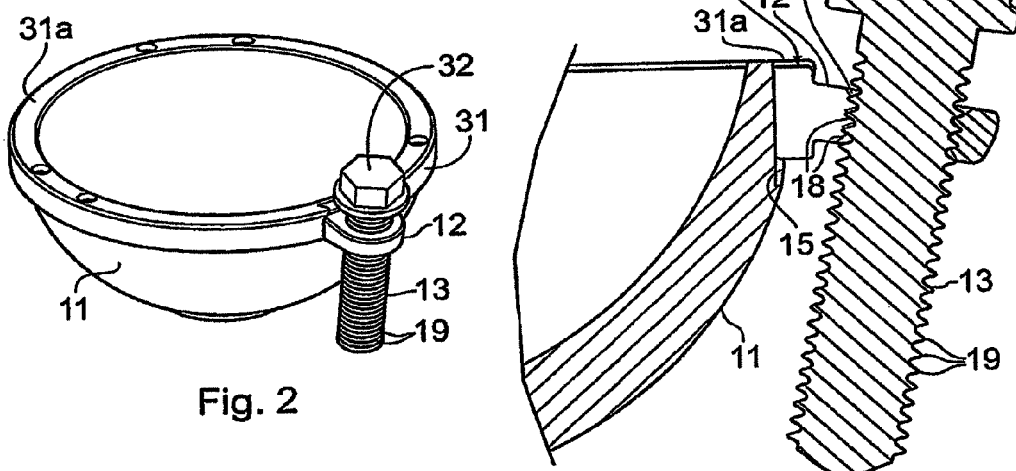
FIG. 2 is a perspective view of the assembled fixing assembly of FIG. 1.
Figure 3:
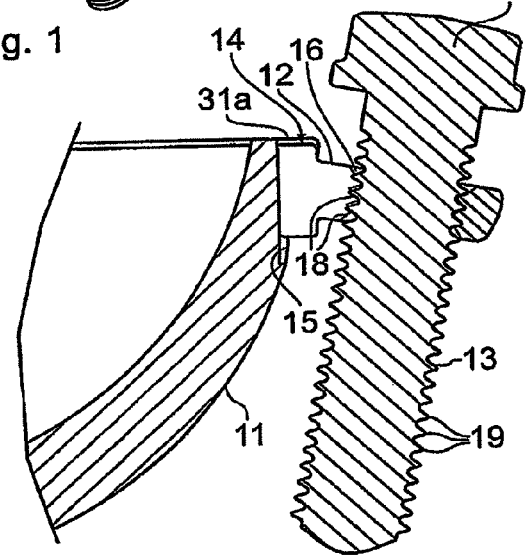
FIG. 3 is an enlarged fragmentary schematic vertical sectional view of the assembled fixing assembly of FIG. 2.
Figure 4:
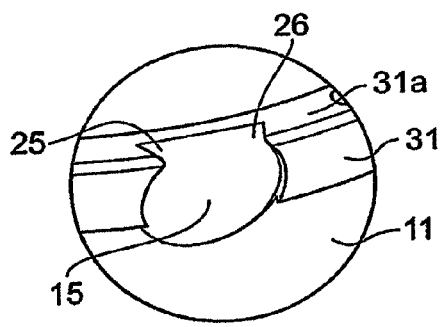
FIG. 4 is an enlarged perspective view of a female location feature as shown in FIGS. 1 to 3.
Figure 5:
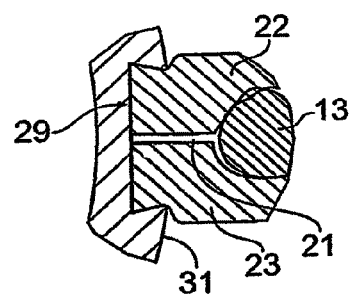
FIG. 5 is an enlarged fragmentary schematic transverse view of the fixing assembly in use, showing detail of the female location feature of the cup, male location feature of the fixing member, and fixing screw of FIGS. 1 to 4.
Figure 6:
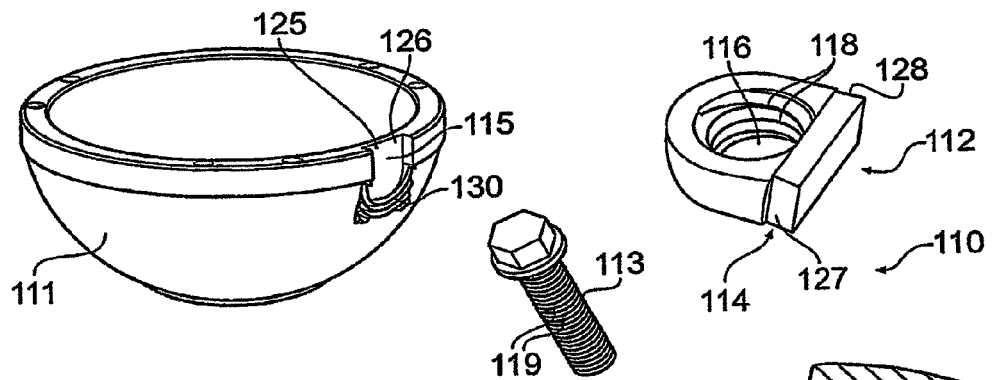
FIGS. 6 to 10 are views corresponding to FIGS. 1 to 5 respectively, showing a second embodiment of the fixing assembly according to the present invention.
Figure 7:
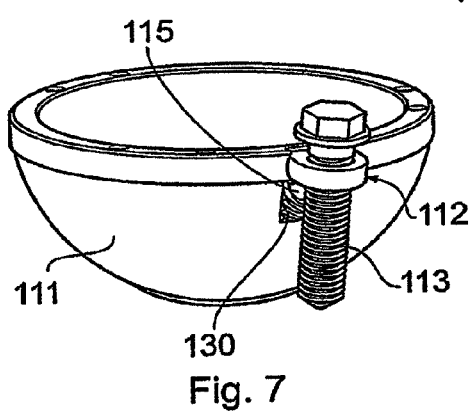
Figure 8:
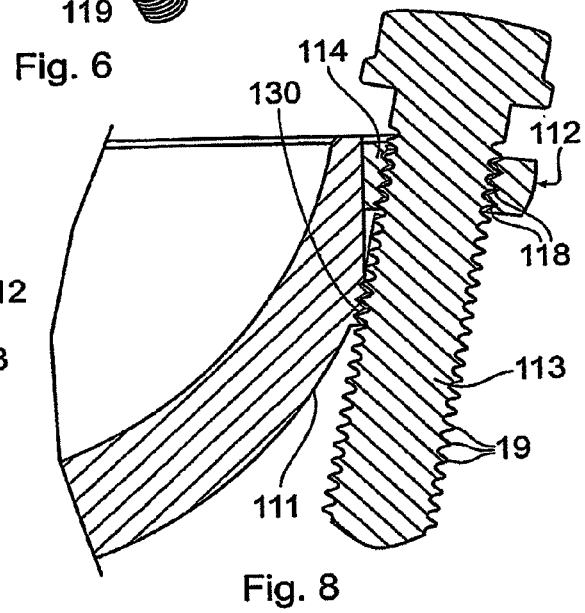
Figure 9:
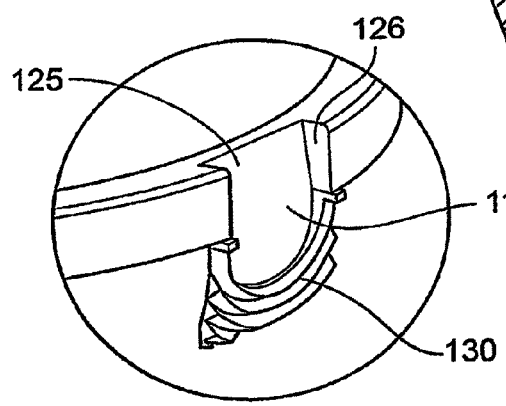

Referring to the drawings, an example embodiment of a fixing assembly 10 according to the present invention is shown in FIGS. 1 to 5. The fixing assembly comprises the external surface of a component, which is an acetabular cup 11 in the preferred embodiment, a fixing member in the form of a lug 12, fixing screw 13 and male and female location features 14 and 15 located on the lug and cup respectively. In use, the fixing assembly secures the lug 12 to the external surface of the cup 11 by means of the male and female location features 14 and 15. Fixing screw 13 passes through an aperture 16 in the lug. Aperture 16 has internal threads 18, which engage with external threads 19 of the fixing screw 13.

The lug 12 has a slit 21, which extends radially from the aperture 16, through said male location feature 14 to divide the male location feature 14 into two arms 22, 23, the relevance of which will be discussed below. The slit is formed in a plane substantially parallel to and including the axis of the aperture.

The location features 14, 15 according to a preferred embodiment of the present invention each have at least one undercut. As can be seen best from FIG. 4, the male location feature 14 of lug 12 has two undercut side portions 27, 28. The female location feature 15 has two corresponding undercut side portions 25, 26 such that, in use, when the male and female location features are fitted together, an interference fit dovetail joint 29 is formed.

In order to assemble the fixing assembly, the male location feature 14 of the lug 12 is inserted into the female location feature 15 of the cup 11. The male location feature 14, and at least part of the remainder of the lug through which the slit extends is made from a suitable material to allow the arms 22, 23 to be slightly pushed or squeezed together during location of the male location feature 14 into the female location feature 15. The slit allows deformation of the male location feature upon the interference fitting of the male and female location features.

The female location feature is a recess in an outer surface of a rim 31 around the exterior of the cup at its open end. The recess breaks through the horizontal surface 31a of the rim and runs out into the external surface of the cup below the rim. The recess is conical (convex) in front view with the undercut side portions 25, 26 each extending from the surface 31a to where the rim runs out. To match the conical (convex) recess, the side of each undercut is correspondingly conical (convex). The male location feature 14 of lug 12 is introduced into the recess forming the female location feature 15 with the lug orientated such that the two corresponding undercut side portions 27, 28 are perpendicular to the axis of the cup. The lug 12 is then attached to the external cup surface 11 by rotating the lug through approximately 90 degrees, so that side portions 27, 28 of the lug 12 engage with undercut side portions 25, 26 of the female location feature 15. The lug may then be articulated to the desired angle by rotation of the lug in its location through a limited angle, the slit 21 allowing for any article manufacturing variations between the interference fit of the male location feature 14 with female location feature 15. In the example of the present invention in the context of an acetabular cup, the fixing screw 13 location point in the bone of a patient (not shown) would be machined conventionally.

The fixing screw 13 is introduced into the lug aperture 16. Fixing screw 13 has a head portion 32, and a thickened portion 33 towards the head, so that when the screw is screwed into the lug aperture 16, the external threads 19 of thickened portion 33 engage with the internal threads 18 of aperture 16, and arms 22, 23 are pushed apart and locked in place by the screw 13. The male location feature of the lug is thus held fixed in position inside the female location feature 15. Unscrewing fixing screw 13 so that the thickened portion 33 is no longer engaged with the aperture 16 allows arms 22, 23 to move together, so that the articulation of the lug 12 may be adjusted relative to the female location feature 15 and thus the surface of the cup 11, or detached from the cup.

Referring to FIGS. 6 to 10, a second embodiment of the fixing assembly 110 according to the present invention comprises an external surface of a component in the form of a cup 111, a fixing member in the form of a lug 112, and a fixing screw 113 and male and female location features 114 and 115 located on the lug and cup respectively. As with the previously described embodiment, in use, the fixing assembly secures the lug 112 to the external surface of the cup 111 by means of the male and female location features 114 and 115. Fixing screw 113 passes through an aperture 116 in the lug. Aperture 116 has internal threads 118, which engage with the external threads 119 of the fixing screw 113.

Figure 10:
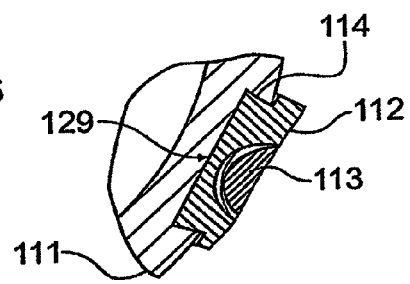
Figure 11:
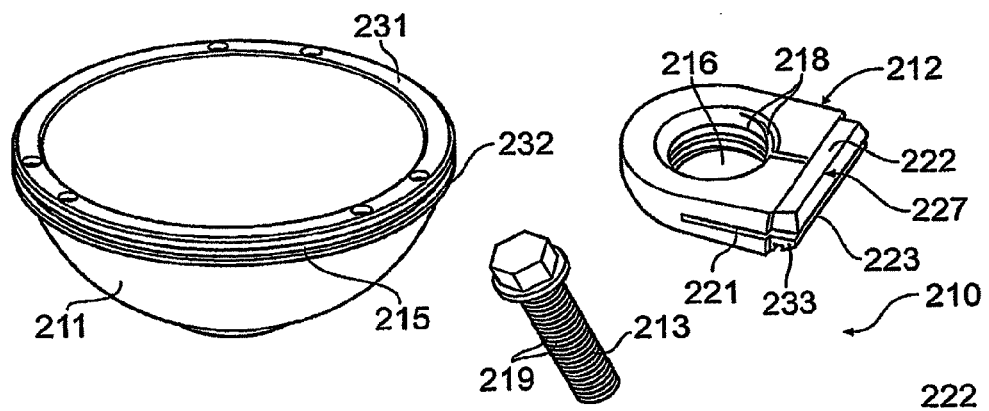
FIGS. 11 to 14 show a third embodiment of the fixing assembly according to the present invention, more specifically.
Figure 12:
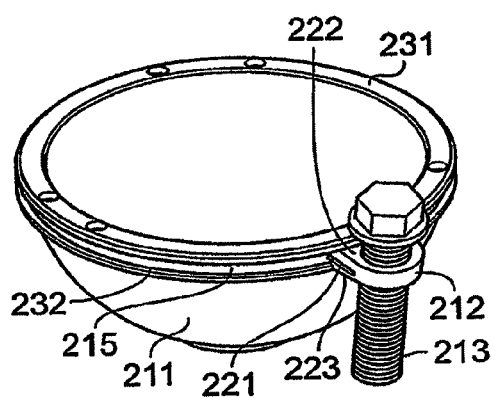
Figure 13:
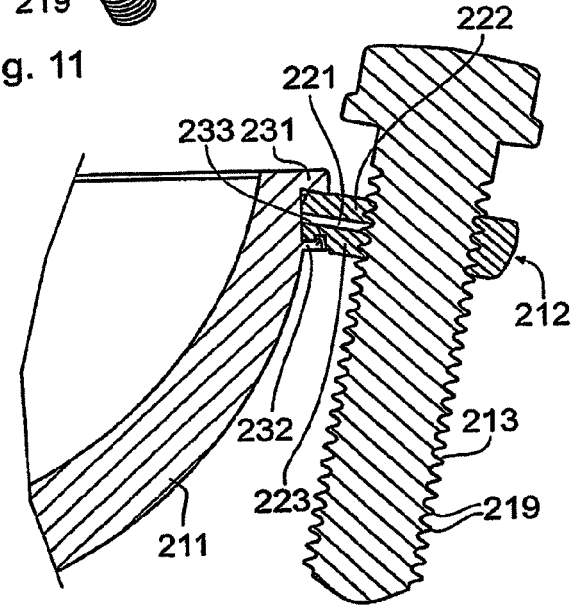

The female location feature 115 is of very similar form to that of the first embodiment, having two undercut side portions 125, 126, and the male location feature 114 has two corresponding undercut side portions 127, 128, such that, in use, when the male and female location features are fitted together, a dovetail joint 129 is formed, as seen best from FIG. 10. However, wherein side portions 27 and 28 of the lug of the first embodiment are conical in profile, side portions 127, 128 of the lug of the second embodiment are prismatic (flat) in profile, and it will be appreciated that undercut portions 125, 126 of the female location feature 115 are correspondingly profiled. It will be appreciated from the illustrations, that the lug herein illustrated and described according to this particular embodiment of the present invention does not feature a slit equivalent to slit 31 of the first embodiment. However, it will be appreciated that such a slit may be incorporated into this embodiment in order to accommodate manufacturing variation.

In use, the male location feature 114 of the lug 112 is slid into the correspondingly formed female location feature 115 of the cup 111. In order to secure the male location feature to the cup, an externally threaded portion 130, with concentric raised threads, is disposed adjacent the female location feature 115 of the cup 111. In the embodiment shown, the threaded portion is disposed on the external surface of the cup 111 directly below the recess forming the female location feature 115. Fixing screw 113 is introduced into lug aperture 116. Although a thickened portion of the fixing screw is not illustrated or described for this particular embodiment of the present invention, it is envisaged that such a thickening may be present. The external threads 119 of the fixing screw 113 engage with the internal threads 118 of the aperture 116, and as the screw 113 is screwed into the aperture, the threads 119 of the fixing screw also engage with those of the complimentarily threaded portion 130 of the external surface of the cup 111. When the screw 113 is screwed into the aperture 116 and engaged with threaded portion 130, the lug 112 is locked in position, attached to the external surface of the cup 111. The threads of portion 130 extend angularly to a sufficient degree to allow engagement of the screw therewith even if the lug is at a slight angle. If the Surgeon wishes to alter the angle of the lug 112 with respect to the cup, an alternative lug (not shown), with its apertured part at an angle to the male location feature, may be employed and fitted as described above.

Referring to FIGS. 11 to 14, a third embodiment of a fixing assembly 210 according to the present invention is shown. The fixing assembly comprises the external surface of a component, which is an acetabular cup 211 in the preferred embodiment, a fixing member 212 in the form of a lug, a fixing screw 213, and male and female location features 214 and 215 located on the lug and cup respectively. As with the previously described embodiments, in use, the fixing assembly secures the lug 212 to the external surface of the cup 211 by means of the male and female location features 214 and 215. Fixing screw 213 passes through an aperture 216 in the lug. Aperture 216 has internal threads 218, which engage with the external threads 219 of the fixing screw 213 which is conventional in form.

The lug 12 has a slit 221, which extends radially from the aperture 216, through said male location feature 214 to divide the male location feature 214 into upper and lower arms 222, 223, the relevance of which will be discussed below. The slit is formed in a plane substantially perpendicular to the axis of the aperture. The external surface of the cup 211 has a circumferential groove 215 defined by upper and lower circumferential ridges 231, 232 respectively, the groove forming the female location feature. This groove 215 has a circumferential undercut portion 225 in the under surface of the upper circumferential ridge 231, for mutual interfit with a correspondingly undercut portion 227 of the upper arm 222 of the male location member 214 of lug 212.

In use, in order to assemble the fixing assembly, the male location feature 214 of the lug 212 is inserted into the groove 215 of the cup 211. The male location feature 214 and the remainder of the lug through which the slit 221 extends, is advantageously made from a resiliently deformable material, and the entire lug may be made from such a resiliently deformable material. Forming the male location feature from a resiliently deformable material enables the arms 222, 223 to be pushed or squeezed together in order to facilitate location of the male location feature 214 into the groove 215. As can be seen best from FIGS. 13 and 14, the undercut portion 225 of the groove is located on the underside of the horizontal surface 231 of the rim of the cup. With the arms 222, 223 squeezed together, the undercut portion 227 of the upper arm 222 of the male location feature 214 of the lug 212 is introduced into the corresponding undercut 225 of the groove 215. The profile of the male location feature 214 is similar in section to that of the groove 215, as can be seen from FIGS. 13 and 14. The lug 212 is then clipped into place by rotating the lug relative to the central axis of the cup, and the pressure on the arms 222, 223 released to allow the arms to separate as far as the profile of the groove will allow. A circumferential outer lip 233 with an upper, outwardly directed arcuate surface 234 is located on the upper surface of the lower circumferential ridge 232. The lower arm 223 of the male location feature of the lug has a downwardly directed ramp 235 with an outwardly facing ramp surface 236. On insertion of the male location feature into the grove 215, the surface 234 engages the surface 236 to move the lower arm upwards. The ramp thus moves past the lip 233, which is then received in a recess 237 of the lower arm disposed behind the ramp. It will be understood that, as an alternative to the specific form of the lug 212 as described and illustrated herein for this particular embodiment, it is envisaged that a folded spring clip may be employed.

Figure 14:
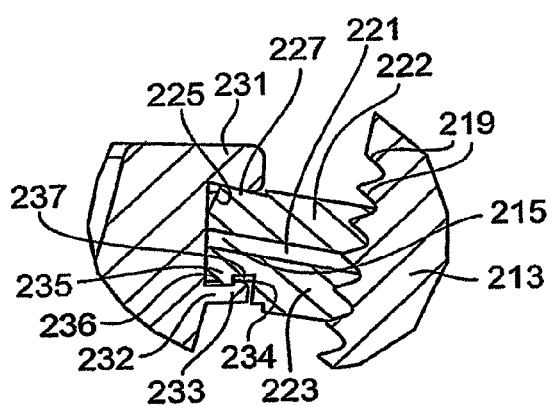

The fixing screw 213 is then introduced into the lug aperture 216. When the screw is screwed into the aperture 216, the external threads 219 engage with the internal threads 218 of the aperture to lock the position of the arms 222, 223 apart, so as to hold the male location feature 214 of the lug 212 in position inside the groove 215, as shown in FIG. 14.

It will be understood that although the example embodiments depict the female location feature 15 on the cup and male location feature 14 on the lug, it is equally possible that the female location feature could be on the lug and the male location feature on the cup, or a combination thereof. In addition, although only one location feature is shown on the cup, it is envisaged that more than one may be present, so that a plurality of lugs may be secured to one cup.

For each of the embodiments described herein, in use, the fixing screw remains external to the surface of the cup, and the fixing screw remains available for use to secure the cup to a second component. In the example of an acetabular cup, this second component would be a patient's bone. Thus it can be seen that the present invention is a particularly convenient arrangement, wherein the fixing screw that secures the fixing means to the external surface of the component is the same fixing screw that may secure the cup to a second component. However, in one alternative the surface could be an internal surface rather than an external one, but with the screw available for securement to a further component.

It is envisaged that a fixing device according to the present invention may be available as a kit form.

Finally, it will be appreciated that a fixing assembly according to the present invention need not relate specifically to an assembly for fixing a lug to an acetabular cup.

It is considered that the component in which the male and/or female location feature(s) is or are provided, such as an acetabular cup, is inventive in its own right.

What is claimed is:

1. A fixing assembly for securing a fixing member to a prosthetic component, the fixing assembly comprising:
   the prosthetic component having either of at least one female location feature or at least one male location feature;
   a fixing member extending outwardly from an outer surface portion of the prosthetic component, the fixing member having the other of the at least one female location feature and the at least one male location feature and a securing member receiving portion; and
   a securing member that cooperates in use with the securing member receiving portion of the fixing member;
   wherein the at least one male and female location features fit together in use and form a first unlocked assembly configuration in which the at least one male and female location features are fitted together and the securing member is not received within the securing member receiving portion of the fixing member and a second locked assembly configuration in which the at least one male and female location features are fitted together and the securing member is received within the securing member receiving portion of the fixing member;
   wherein the fixing member is free to rotate in an orbital manner at least partially around the prosthetic component in the first unlocked assembly configuration;
   wherein the fixing member prevents relative rotation between the fixing member and the prosthetic component in the second locked assembly configuration;
   wherein the prosthetic component is an acetabular cup; and
   wherein the at least one female location feature comprises an undercut groove portion and the at least one male location feature comprises a flared portion forming a dovetail that is received within the undercut groove portion.

2. The fixing assembly of claim 1, wherein the undercut groove portion extends around at least part of the outer surface portion of the prosthetic component.

3. The fixing assembly of claim 1, wherein the dovetail enables rotation of the fixing member relative to the prosthetic component when the securing member is not received within the securing member receiving portion of the fixing member.

4. The fixing assembly of claim 1, wherein the at least one male location feature comprises a plurality of arms, each of which arms is separated from another of the arms by at least one slit.

5. The fixing assembly of claim 4, wherein the at least one male location feature comprises a deformable material.

6. The fixing assembly of claim 4, wherein the slit extends radially from the fixing member.

7. The fixing assembly of claim 4, wherein the at least one male location feature further comprises a biasing element to push apart each of the arms from another of the arms.

8. The fixing assembly of claim 7, wherein the biasing element is a spring clip.

9. The fixing assembly of claim 1, wherein the at least one male location feature is located on the fixing member.

10. The fixing assembly of claim 1, wherein the at least one location feature of the prosthetic component is at least partly located on a rim of the outer surface portion of the prosthetic component.

11. The fixing assembly of claim 1, wherein the outer surface portion of the prosthetic component includes at least one circumferential groove that forms the at least one female location feature to lock the fixing member to the prosthetic component.

12. The fixing assembly of claim 11, wherein the at least one circumferential groove comprises a plurality of circumferential grooves.

13. The fixing assembly of claim 1, wherein the at least one location feature of the prosthetic component comprises a plurality of location features.

14. A fixing assembly for securing a fixing member to a prosthetic component, the fixing assembly comprising:
   the prosthetic component having either one of a female location feature or a male location feature;
   a fixing member extending outwardly from an outer surface portion of the prosthetic component, the fixing member having the other of the female location feature and the male location feature; and
   wherein the male and female location features fit together in use;
   wherein the female location feature comprises at least one undercut groove portion and the male location feature comprises at least one flared portion forming at least one dovetail that is received within the at least one undercut groove portion;
   wherein the fixing member is free to rotate in an orbital manner about a rim of the prosthetic component when the at least one dovetail is in a disengaged condition and when the male and female location features are fitted together;
   and wherein an interaction between the at least one dovetail of the male location feature and the at least one undercut groove portion of the female location feature prevents relative rotation between the fixing member and the prosthetic component when the at least one dovetail is in an engaged position with respect to the at least one undercut groove portion of the female location feature.

15. The fixing assembly of claim 14, wherein the at least one undercut groove portion extends around at least part of the outer surface portion of the prosthetic component.

16. The fixing assembly of claim 14, wherein the male location feature comprises a plurality of arms, each of which arms is separated from another of the arms by at least one slit.

17. The fixing assembly of claim 16, wherein the male location feature comprises a deformable material.

18. The fixing assembly of claim 16, wherein the slit extends radially from the fixing member.

19. The fixing assembly of claim 14, wherein the male location feature is located on the fixing member.

20. The fixing assembly of claim 14, wherein the location feature of the prosthetic component is at least partly located on a rim of the outer surface portion of the prosthetic component.

21. The fixing assembly of claim 14, wherein the outer surface portion of the prosthetic component includes at least one circumferential groove that forms the female location feature to lock the fixing member to the prosthetic component.

22. The fixing assembly of claim 21, wherein the at least one circumferential groove comprises a plurality of circumferential grooves.

23. The fixing assembly of claim 14, wherein the component is an acetabular cup.

24. The fixing assembly of claim 14, wherein the at least one undercut groove portion of the female location feature comprises a plurality of undercut groove portions.

* * * * *